(12) United States Patent
Gutman

(10) Patent No.: US 7,976,777 B2
(45) Date of Patent: Jul. 12, 2011

(54) METHOD FOR AN AGENT CONTAINING PACKAGE

(76) Inventor: Jose Gutman, Boca Raton, FL (US)

( * ) Notice: Subject to any disclaimer, the term of this patent is extended or adjusted under 35 U.S.C. 154(b) by 1220 days.

(21) Appl. No.: 11/226,123

(22) Filed: Sep. 13, 2005

(65) Prior Publication Data

US 2006/0008400 A1    Jan. 12, 2006

Related U.S. Application Data

(63) Continuation-in-part of application No. 10/167,927, filed on Jun. 10, 2002, now Pat. No. 6,942,834.

(51) Int. Cl.
*A61L 2/00* (2006.01)

(52) U.S. Cl. .................. 422/24; 422/186.3; 422/186.07; 250/455.11

(58) Field of Classification Search .................. 422/24, 422/186, 186.07, 186.3; 250/455.11
See application file for complete search history.

(56) References Cited

U.S. PATENT DOCUMENTS

| | | | |
|---|---|---|---|
| 4,919,955 A | 4/1990 | Mitchell | |
| 5,011,699 A | 4/1991 | Mitsuda et al. | |
| 5,213,759 A | 5/1993 | Castberg et al. | |
| 5,227,184 A | 7/1993 | Hurst | |
| 5,352,467 A | 10/1994 | Mitchell et al. | |
| 5,405,671 A | 4/1995 | Kamin et al. | |
| 5,413,757 A | 5/1995 | Kutner et al. | |
| 5,460,269 A | 10/1995 | Bayer | |
| 5,597,599 A | 1/1997 | Smith et al. | |
| 5,618,492 A | 4/1997 | Auten et al. | |
| 5,869,159 A | 2/1999 | Padilla | |
| 5,932,322 A | 8/1999 | Jones et al. | |
| 6,085,492 A | 7/2000 | Moller et al. | |
| 6,342,187 B1 | 1/2002 | Jacob et al. | |
| 6,403,033 B1* | 6/2002 | Gutman | 422/29 |
| 6,429,438 B1* | 8/2002 | Smestad | 250/373 |
| 6,514,405 B1* | 2/2003 | Lifschitz | 210/143 |
| 6,607,672 B2 | 8/2003 | Koslow et al. | |
| 6,656,424 B1* | 12/2003 | Deal | 422/3 |
| 6,712,276 B1 | 3/2004 | Abali et al. | |
| 6,720,866 B1 | 4/2004 | Sorrells et al. | |
| 6,767,453 B2* | 7/2004 | Lifschitz | 210/85 |
| 6,784,440 B2 | 8/2004 | Fink et al. | |
| 6,806,808 B1 | 10/2004 | Watters et al. | |

(Continued)

OTHER PUBLICATIONS

International Search Report dated May 23, 2007 for PCT/US 06/35566.

(Continued)

*Primary Examiner* — Sean E Conley
(74) *Attorney, Agent, or Firm* — Jose Gutman

(57) ABSTRACT

A method, a sensor device (204), and a package storage system (200), are used to monitor the inside of a storage volume in a package container (202) containing at least one product and/or object (201). The sensor device is inside of the storage volume in the package container (202) and senses the presence of at least one of a sanitizing agent comprising ozone (316) and ultraviolet radiation energy inside of the storage volume. The sensor device (204) wirelessly transmits the sensed information from inside the at least one storage volume to a wireless receiver (222) outside of the storage volume to provide the sensed information to a processor (220) that monitors the presence of the at least one of the sanitizing agent comprising ozone (316) and ultraviolet radiation energy inside of the storage volume in the package container (202). The sensor device (204) can communicate using an RF ID device communication protocol.

20 Claims, 9 Drawing Sheets

U.S. PATENT DOCUMENTS

| | | | |
|---|---|---|---|
| 6,942,834 B2 * | 9/2005 | Gutman | 422/29 |
| 7,160,566 B2 | 1/2007 | Fink et al. | |
| 7,238,076 B2 | 7/2007 | Yoshida et al. | |
| 7,258,882 B2 | 8/2007 | Hankinson et al. | |
| 2002/0122743 A1 | 9/2002 | Huang | |
| 2002/0150500 A1 | 10/2002 | Carman et al. | |
| 2002/0155027 A1 | 10/2002 | Gutman | |
| 2002/0168287 A1 | 11/2002 | Eckhardt et al. | |
| 2003/0086818 A1 | 5/2003 | Holley et al. | |
| 2003/0086821 A1 | 5/2003 | Matthews | |
| 2003/0127506 A1 * | 7/2003 | Braun, Jr. | 232/31 |
| 2005/0186124 A1 | 8/2005 | Fink et al. | |
| 2006/0144690 A1 | 7/2006 | Fink et al. | |
| 2006/0266221 A1 | 11/2006 | Fink et al. | |
| 2007/0110860 A1 | 5/2007 | Fink et al. | |

OTHER PUBLICATIONS

Steve Lewis, "A Basic Introduction to RFID Technology and its use in the Supply Chain", Laran RFID; Jan. 2004, www.laranrifid.com (5 pages).

* cited by examiner

METHOD FOR AN AGENT CONTAINING PACKAGE

CROSS-REFERENCE TO RELATED APPLICATIONS

This application is a continuation-in-part of, and claims priority from, prior U.S. patent application Ser. No. 10/167,927, filed on Jun. 10, 2002, now assigned U.S. Pat. No. 6,942,834, the entire disclosure of which is herein incorporated by reference, and wherein such co-pending prior application was based upon, and claimed priority from, prior U.S. patent application Ser. No. 09/583,041, filed on May 30, 2000, now assigned U.S. Pat. No. 6,403,033, the entire disclosure of which is also herein incorporated by reference, and wherein such prior application was based upon, and claimed priority from, prior U.S. Patent Application No. 60/136,885, filed on Jun. 1, 1999, now expired, the entire disclosure of which is also herein incorporated by reference.

FIELD OF THE INVENTION

The present invention generally relates to using ozone to provide at least one of a sanitizing, disinfecting, and sterilizing, application to an object or product, and more particularly to a system and method for monitoring ozone and ultraviolet radiation energy in-package for providing and containing a sanitizing agent comprising ozone gas in a packaging structure for an object or product to thereby transfer the sanitizing agent comprising ozone gas to the object or product while being located in the packaging structure and thereby to prolong the at least one of sanitizing, disinfecting, and sterilizing, effect to the object or product in the packaging structure.

BACKGROUND OF THE INVENTION

Objects or products such as perishable food products, including meats, poultry, fish, fruits, and vegetables, or objects such as medical devices and instruments, or other objects that may be subject to infection or contamination by micro-organisms, viruses, and pathogens, typically require hygienic and sanitary conditions to be properly handled, packaged, and/or used. These types of objects or products are generally susceptible to contamination from micro-organisms such as bacteria, and from viruses, pathogens, and from other similar unsanitary contaminants. These objects are regularly subject to environmental exposure to contaminants such as micro-organisms, viruses, and other such contaminants thereby degrading sanitary and hygienic conditions for the objects or products.

Food products, for example, can seriously degrade in shelf life and can be dangerous for consumption under unsanitary states. Medical devices and instruments are likewise subject to contamination from many sources and can cause serious harm if used in unsanitary conditions. Cuts and wounds and other conditions of the body of animals and humans are similarly susceptible to external biological contaminants and micro-organisms and pathogens under unsanitary conditions which can cause infection, disease and other serious consequences if left unattended.

In the past, attempts to sanitize these types of objects have generally included washing and cleansing an object and then packaging and/or wrapping the object, which normally took place in special clean processing facilities. However, it is not always feasible or desirable to set up significant special facilities to sanitize such objects to desirable levels. For example, it may be desirable to package and/or wrap a food product at a convenient location where no special facilities are normally available such as at an office, a home, or even outdoors. Similarly, it may be desirable to package and/or wrap a medical device or instrument with no special medical cleansing facility being available or desirable for sanitizing the medical instrument before a subsequent use.

Regrettably, in most circumstances after providing sanitizing agents and cleansing facility to help clean and sanitize a product or object, subsequent poor handling by personnel typically results in re-contamination prior to final packaging of the product or object. This poor handling creates serious contamination hazards and transfer of disease to users and consumers of the products and objects being packaged under such conditions. Most commonly, an expensive special handling and processing facility is required to provide a sanitizing and/or sterilizing effect to an object or product. For example, irradiation processing of object and products requires very specialized and expensive equipment that is not readily usable in most environments.

With respect to perishable food products, such as meat, poultry, or fish, such products are normally packaged and re-packaged for subsequent use or distribution where at each stage of unpacking and re-packaging there is potential for introduction of contaminants, such as micro-organisms and viruses, and other pathogens, such as from *E-coli*, salmonella, and listeria contamination, that can harm humans as well as seriously degrade the shelf life, increase perishability, and detrimentally impact human consumability, of such food products. The normal handling conditions at the different stages of product distribution, ultimately to handling by an end user, and further the re-packaging at each one of the stages, causes additional risk for contamination of such food products.

Additionally, for providing sanitizing and/or sterilizing treatments to products and objects to be packaged and/or while packaged, it is desirable to expose the surfaces of the products and objects to the treatments. Surfaces of the multiple products and/or objects that remain unexposed to sanitizing and/or sterilizing treatments may likely continue to carry contaminants, including microbes such as bacteria and viruses, that continue to pose contamination hazards to users and consumers of the products and/or objects. Therefore, sanitizing and/or sterilizing treatments that fail to treat the surfaces may not remove the necessary amount of contamination to result in desired sanitary and/or sterile conditions for the packaged products and/or objects. Unfortunately, a lack of treatment may not be detected after the products and/or objects are packaged. The contaminated products and/or objects after being packaged unfortunately may reach the user and/or consumer.

Food products, therefore, can include contaminants such as all sorts of micro-organisms, bacteria, and viruses. These contaminants can include, but are not limited to, bacteria, fungi, yeast, mold, mildew, and a variety of viruses. *E-coli* and listeria are pathogens that have gained much attention in the news where humans have been made sick and injured and have died as a result of contamination of food and water. Many of these types of contaminants can increase a rate of spoilage and reduce shelf life of food products as well as provide serious health hazards to humans that consume or come in contact with such products. Commonly, these contaminants are introduced to the surfaces of food products during processing, handling, and distribution.

Modern methods of packaging and cleaning food products, typically employed at food processing plants and factories, can reduce hazardous contaminants, such as micro-organisms, that can contaminate the surfaces of food products.

These processing and packaging techniques include thermal processing, washing food products with chlorinated water, irradiation of food products, vacuum sealing packaging, low temperature storage, modified atmosphere packaging (or MAP), active packaging, and certain techniques for clean handling and packaging. Additionally, ozone bubbled in water has been used to wash and thereby disinfect chickens and other such food products and associated food processing plants and such specialized food handling environments. Ozone in such aqueous solution has been generally regarded as safe for use with the food supply. For example, most people are familiar with ozonated drinking water. However, these processes and techniques discussed above typically must be applied under strictly controlled environments in a processing plant and factory and usually employing special equipment and handling.

These specialized requirements for packaging such food products, although helpful in reducing contamination and enhancing shelf life of products, are generally expensive and only available in special environments such as in food processing plants and factories. Further, when the packaging is removed at a later point in a distribution channel and the food product is re-packaged for further distribution or for consumption at a later time, new contamination can typically be introduced to the food products thereby losing some if not most of the beneficial effects of the earlier clean handling and packaging at the factory. This subsequent re-packaging and handling normally does not benefit from special equipment and ultra-clean environment to re-package the food products with heightened sanitary conditions as in a food processing plant and factory.

In medical applications, where medical equipment and instruments need to be sanitized, unfortunately, conventional specialized equipment must be used to sanitize and disinfect the equipment or instruments to a satisfactory level, or possibly sterilize as necessary, for further use. This specialized equipment is usually expensive and the process for sanitizing, disinfecting, and/or sterilizing, tends to be time consuming significantly impacting the costs of medical services and the commercial viability of medical businesses. Additionally, this specialized equipment and processing is normally not generally available in all but specialized environments.

Accordingly, there is a need for a system and method to eliminate the disadvantages of the prior art as discussed above, and particularly to provide a sanitizing, disinfecting, and/or sterilizing, application to objects and/or products being packaged.

BRIEF DESCRIPTION OF THE DRAWINGS

The accompanying figures where like reference numerals refer to identical or functionally similar elements throughout the separate views and which together with the detailed description below are incorporated in and form part of the specification, serve to further illustrate various embodiments and to explain various principles and advantages all in accordance with the present invention.

DETAILED DESCRIPTION

Figure 1:
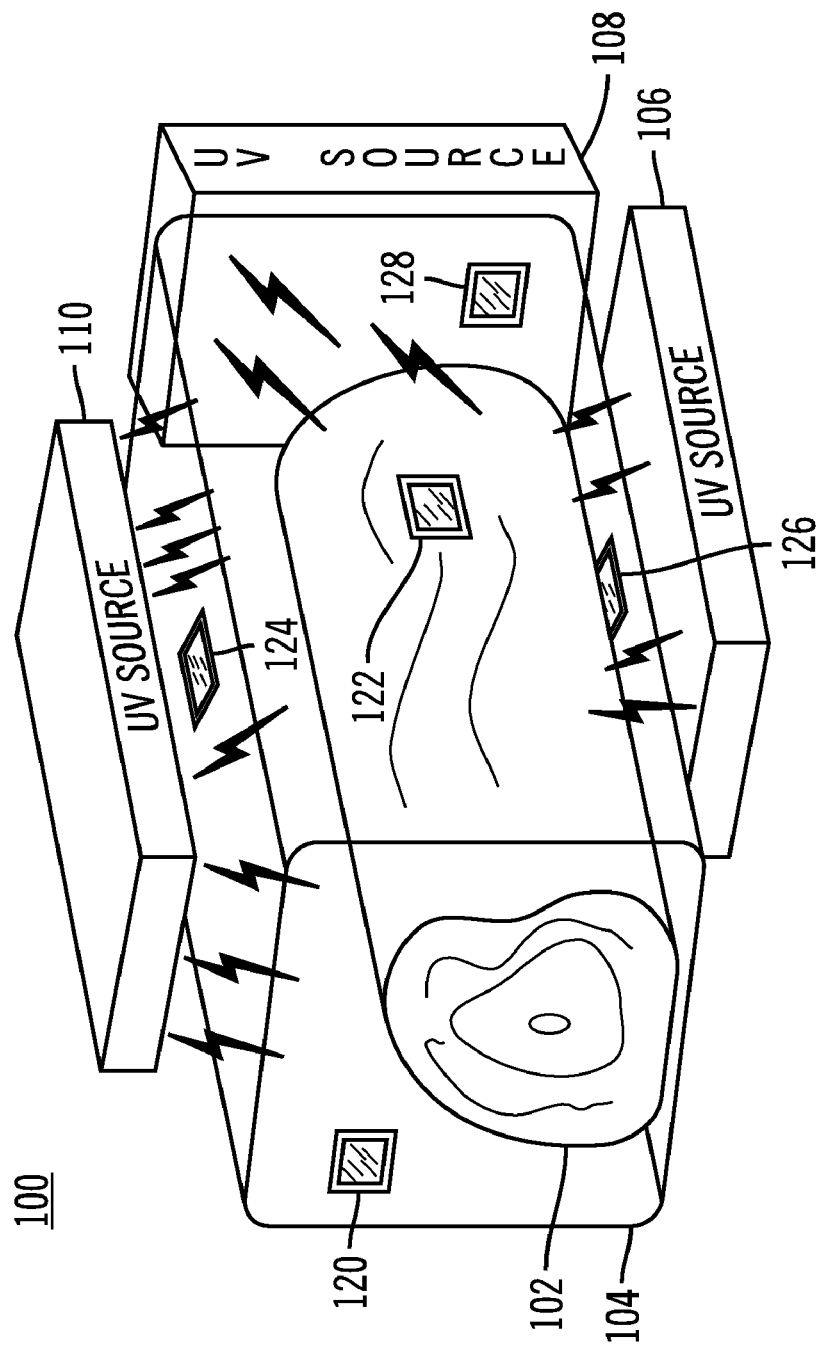
FIG. 1 is a perspective view of an exemplary self-monitoring packaging system according to an embodiment of the present invention.

As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically.

The present invention, according to an embodiment, overcomes problems with the prior art by providing an The terms program, software application, and the like as used herein, are defined as a sequence of instructions designed for execution on a computer system. A program, computer program, or software application typically includes a subroutine, a function, a procedure, an object method, an object implementation, an executable application, an applet, a servlet, a source code, an object code, a shared library/dynamic load library and/or other sequence of instructions designed for execution on a computer system.

While the specification concludes with claims defining the features of the invention that are regarded as novel, it is believed that the invention will be better understood from a consideration of the following description in conjunction with the drawing figures, in which like reference numerals are carried forward.

The present invention overcomes problems with the prior art by providing a means for monitoring the inside of a package container to determine the presence of at least one of a sanitizing agent comprising ozone and ultraviolet radiation energy thereby monitoring the exposure of a product and/or object in the package container to the at least one of the sanitizing agent comprising ozone and the ultraviolet radiation energy. The exposure of the object or product to a sanitizing agent comprising ozone gas and/or to ultraviolet radiation energy in the storage volume in the package container effectively provides sanitizing, disinfecting, and sterilizing, treatment to the object or product captured or stored in at least one storage volume of the package container. However, by affirmatively monitoring this exposure inside the package container enhances the overall process to provide sanitizing, disinfecting, and sterilizing, treatment to the object or product.

Further, the term sanitizing agent comprising ozone gas is generally used herein to describe an agent that when transferred to a surface of an object or product at least provides the beneficial sanitizing, disinfecting, and sterilizing effects provided by ozone gas. Ozone gas has been shown very effective to sanitize, disinfect and sterilize equipment and processing facilities, as well as for ozonating drinking water. Ozone, in varying concentrations as a treatment for products and objects, can provide beneficial sanitizing, disinfecting, and sterilizing, effects thereto.

Shortly after treatment, the ozone normally converts to a harmless composition usually resulting in oxygen associated with a treated product or object. For example, ozonated water additionally benefits from enhanced taste for human consumption.

The sanitizing agent comprising ozone gas, according to an embodiment of the present invention, provides at least a reduction in microbial count as part of a sanitizing application. Further, in certain applications, such as for medical sanitizing or other product sanitizing, the sanitizing agent comprising ozone gas can provide anti-viral and anti-pathogen properties to attack contaminants comprising viruses and other pathogens. Therefore, as anticipated by the embodiments of the present invention, and in accordance with specific applications thereof, the sanitizing agent comprising ozone gas provides anti-microbial properties to reduce microbial counts, including but not limited to reduction in bacteria, fungi, yeast, mold, and mildew, counts. Further, the sanitizing agent comprising ozone gas, according to alternative preferred embodiments of the present invention used in certain applications, additionally provides anti-viral properties to attack certain viruses. As is well known, ozone can exhibit such beneficial anti-microbial properties and anti-viral properties for specific applications of the embodiments of the present invention. Accordingly, the term sanitizing agent is used herein to comprise properties that can sanitize and disinfect, i.e., reduce microbial and viral counts, and/or sterilize, i.e., substantially minimizing counts thereof, with respect to an object or product being sanitized by the sanitizing agent comprising ozone gas and in accordance with specific applications. The term contaminants as used herein, therefore, includes such microbial and viral contaminants, and generally other invading contaminants, that can create unsanitary conditions, spoilage, and/or damage to objects or products. Additionally, it should be clear that the sanitizing agent comprising ozone provides beneficial sanitizing, disinfecting, and sterilizing effect while in close proximity to a surface of an object or product.

As shown in FIG. 1, an exemplary package storage system 100 is shown. A product or object 102 is contained in at least one storage volume in a package container 104. The package container 104 in this example comprises a plastic film packaging structure that provides a barrier and protection from outside contaminants while allowing ultraviolet radiation energy to pass through at least a portion of the packaging structure and into an internal storage volume. The ultraviolet radiation energy, in the current example, is radiated from one or more ultraviolet energy sources 106, 108, 110, and through the packaging structure of the packaging container 104, and into the at least one storage volume that contains the product or object 102.

Additionally, one or more sensor devices 120, 124, 126, 128, are located inside the packaging container 104, such that the presence of a sanitizing agent comprising ozone may be detected in the at least one storage volume that contains the product or object 102. These sensor devices 120, 124, 126, 128, according to an example, also detect the presence of ultraviolet radiation energy in the at least one storage volume. The particular frequency range and energy of the detected ultraviolet radiation energy can also be of interest for particular applications. The structure and function of various embodiments of the sensor devices 120, 124, 126, 128, will be discussed in more detail below.

Figure 2:
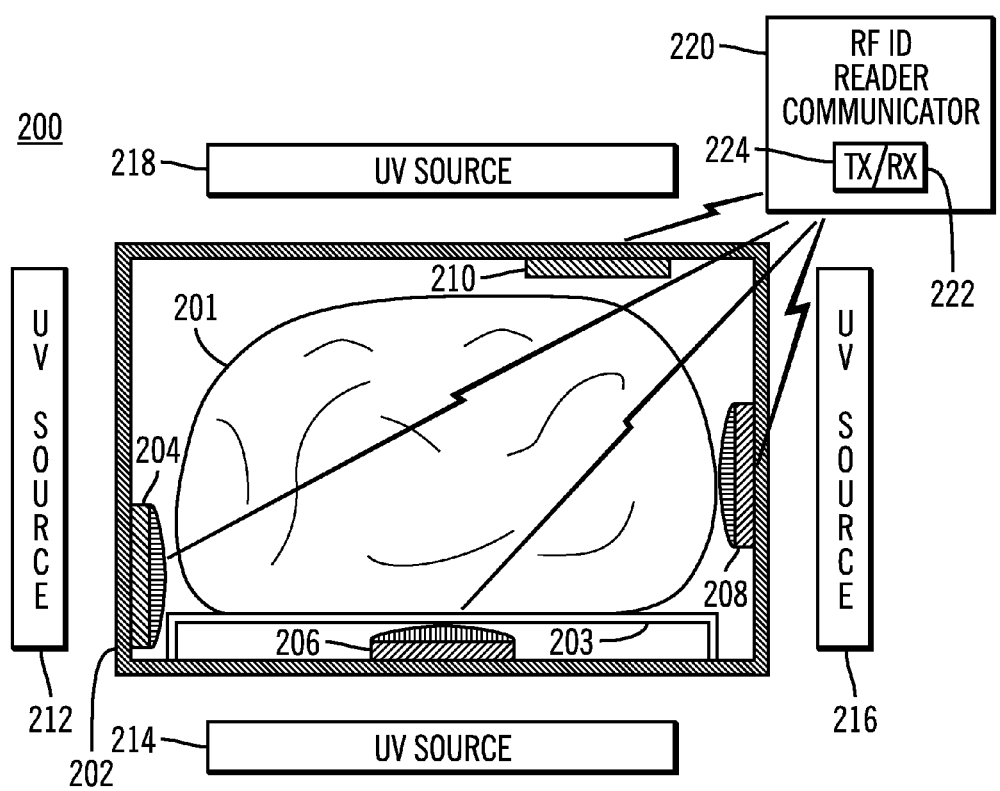
FIG. 2 is a cross-sectional side view of an exemplary self-monitoring packaging system with an RF reader and communicator according to an embodiment of the present invention.

Referring to FIG. 2, a package storage system 200 is shown with a product or object 201 contained in a storage volume in a package container 202. A plurality of ultraviolet radiation energy sources 212, 214, 216, 218, are shown in an orientation and proximity to radiate ultraviolet radiation energy through the packaging structure of the package container 202 and into the storage volume inside the package container 202. In this way, when the ultraviolet radiation energy sources 212, 214, 216, 218, are energized at a first state, a first agent comprising oxygen in the storage volume is converted to a sanitizing agent comprising ozone. For example, ultraviolet radiation energy at about 185 nm can energizably convert a first agent comprising oxygen in the storage volume to a sanitizing agent comprising ozone. Additionally, when the ultraviolet radiation energy sources 212, 214, 216, 218, are energized at a second state, the sanitizing agent comprising ozone in the storage volume is converted to the first agent comprising oxygen. For example, ultraviolet radiation energy at about 253 nm can energizably convert the sanitizing agent comprising ozone in the storage volume to the first agent comprising oxygen. Additionally, a substantially 253 nm wavelength range for the ultraviolet radiation energy provides a strong anti-microbial killing treatment of ultraviolet radiation energy to the product or object 201 contained in the storage volume in the package container 202.

Hence, for example, for a first time period while the ultraviolet radiation energy is radiated in the environment in the storage volume at a first frequency, such as at about 253 nm wavelength range for ultraviolet radiation energy, the surfaces within the environment in the storage volume, such as all the exposed surfaces of the product or object 201 and the surfaces of the package container 202, are exposed to strong anti-microbial killing ultraviolet radiation energy. At a second time interval, the ultraviolet radiation energy radiated from the ultraviolet radiation energy sources 212, 214, 216, 218, comprises ultraviolet radiation energy that is substantially a frequency of about 185 nm wavelength range. This ultraviolet radiation energy at about 185 nm wavelength range will energize a convertible first agent comprising oxygen and convert it to the sanitizing agent comprising ozone. The sanitizing agent comprising ozone has a strong lingering effect for killing microbes that may be resident on the exposed surfaces of the product or object 201, and the exposed surfaces of the package container 202. The sanitizing agent comprising ozone provides additional sanitizing and/or sterilizing effect to the packaged product or object 201 in the container 202.

During storage in the package storage system 200, the storage volume in the container 202 contains an atmosphere and environment that can be additionally treated by ultraviolet radiation energy to alternatively provide the anti-microbial killing ultraviolet energy frequency to the surfaces exposed within the container 202 while converting any sanitizing agent comprising ozone in the container 201 back to the convertible first agent comprising oxygen. Then, at a second ultraviolet radiation energy frequency the convertible agent comprising oxygen in the storage volume in the container 202 can be converted to the sanitizing agent comprising ozone to provide additional sanitizing and/or sterilizing treatment to the packaged product and/or object 201. This dual action treatment provides significant long term sanitizing and/or sterilizing effect to the packaged product and/or object 201 that will then remain packaged in the sealed container 202 until ready to be used and/or consumed by a user. Advantageously, all surfaces of products and/or objects can be exposed to both the ultraviolet energy with anti-microbial killing effect and further to the sanitizing agent comprising ozone that provides additional long term sanitizing and/or sterilizing effect to the products and/or objects in the storage volume in the package 202. Note that this treatment can be applied to many different types of products and/or objects being packaged such as in the food industry, medical industry, instrumentation industry, pharmaceutical industry, and such other fields of use that benefit from applying sanitizing and/or sterilizing treatment to products and/or objects contained in package containers, as should be obvious to those of ordinary skill in the art in view of the present discussion.

It is a well known principle that ozone gas can be formed from oxygen gas by increasing the energy of the oxygen to create the ozone gas. The general process of converting oxygen gas to ozone gas is a well understood process. By using an energy source, such as an ultraviolet radiation energy source or an electrical corona discharge radiation energy source, oxygen gas can efficiently and relatively quickly (in seconds) be converted to ozone gas. Accordingly, an energy source that converts oxygen to ozone, as anticipated by those of ordinary skill in the art, may be usable in accordance with the preferred embodiments of the present invention. Additionally, the oxygen gas and the ozone gas may exist in a gas atmosphere, and alternatively in a fluid atmosphere, in the at least one store. Accordingly, an agent contained in the at least one store may comprise gas, and alternatively fluid, that includes the oxygen for conversion to the ozone. The oxygen can be energized and converted to ozone in the at least one store. A first agent comprising oxygen can be energized by the energy source as discussed above to provide the sanitizing agent comprising ozone in the at least one store.

Continuing with the current example, as shown in FIG. 2, the product and/or object 201 is shown optionally located on a supporting stand 203. The supporting stand 203 comprises an open pattern grill along the supporting surface of the stand 203 that supports a bottom surface of the product and/or object 201. In this way, according to the present example, there is storage volume space below the bottom surface of the product and/or object 201 in the package container 202. The bottom surface of the product and/or object 201 therefore is supported away from an inner surface of the package container 202 thereby substantially exposing the bottom surface of the product and/or object 201 to an environment in the storage volume in the package container 202. The environment in the storage volume contains a convertible first agent comprising oxygen that can energizably convert to a sanitizing agent comprising ozone. The bottom surface of the product and/or object 201 can be exposed to the sanitizing agent comprising ozone.

Optimally, the surfaces of the product and/or object 201 are all substantially exposed to at least one of the sanitizing agent comprising ozone and/or to the ultraviolet radiation energy. In the event that a surface of the product and/or object 201 is substantially contacting an inner surface of the packaging structure of the storage volume in the package container 202, at least the anti-microbial ultraviolet radiation energy, comprising ultraviolet radiation energy at about 253 nm frequency range, can radiate these exposed surfaces of the product and/or object 201 with strong anti-microbial killing ultraviolet radiation energy. Additionally, other surfaces of the product and/or object 201 that are not in substantial contact with the inner surface of the packaging structure of the storage volume in the package container 202 will be exposed to both the anti-microbial ultraviolet radiation energy, comprising ultraviolet radiation energy at about 253 nm frequency range, and to the sanitizing agent comprising ozone, which is created in the storage volume by converting the convertible first agent comprising oxygen to the sanitizing agent comprising ozone by radiating the environment in the storage volume inside the package container 202 with ultraviolet radiation energy at about 185 nm frequency range. Therefore, all exposed surfaces of the product and/or object 201 in the storage volume will be treated with anti-microbial treatment to provide a sanitizing, disinfecting, and/or sterilizing treatment to the product and/or object 201.

Note that in prior art packaging methods and systems, such as using modified atmosphere packaging (MAP) or active packaging, a food product is introduced into a package and then a modified atmosphere is introduced into the package upon seal. The modified atmosphere typically is introduced by some form of injection or similar process after the product has been packaged. This, unfortunately, has the consequence that normally only a certain portion of the product is exposed to the modified atmosphere upon packaging. This is mainly due to the product being pre-packaged in a container and then the modified atmosphere being introduced from one side, usually the top side, of the packaging thereby exposing only that immediate side of the product to the modified atmosphere. However, other significant sides of the package and food product are normally not immediately exposed to the modified atmosphere. The modified atmosphere generally has to travel through the packaged product to reach some of the other surfaces of the product. Therefore, any contaminants on surfaces of the product not directly exposed to the modified atmosphere may not be significantly affected by the modified atmosphere.

Also as shown in FIG. 2, a plurality of sensor devices 204, 206, 208, 210, are located in the storage volume containing the product and/or object 201. Each of these sensor devices 204, 206, 208, 210, can be used to monitor the internal environment of the storage volume in the package container 202. For example, the presence of sanitizing agent comprising ozone and/or the presence of ultraviolet radiation energy may be monitored by one or more of these sensor devices 204, 206, 208, 210, as will be discussed in more detail below. Note also that the sensor devices 204, 206, 208, 210, may include an optional open space grill cover, such as illustrated for the three sensor devices 204, 206, and 208. This open space grill cover allows some spacing between the sensor devices 204, 206, 208, and the surface of the product and/or object 201 thereby providing a space in the storage volume for the particular sensor devices 204, 206, 208, to sense the presence of sanitizing agent comprising ozone in the environment in the storage volume in proximity to the surface of the product and/or object 201. Additionally, in some applications, certain sensor devices, such as the one sensor device 210 located at the top of the storage volume, may not need to include an open space grill cover because the location and orientation of the sensor device 210 under anticipated use in a package container 202 will normally result in having an open space environment between the sensor device 210 and the surface of the product and/or object 201.

One or more of the sensor devices 204, 206, 208, 210, may also include a wireless transmitter circuit (not shown in FIG. 2) that allows the sensor devices 204, 206, 208, 210, to transmit information to a wireless communication device 220 that can receive the transmitted information. For example, such a wireless communication device 220 may comprise a wireless reader device 220 that can optionally include a receiver 222, a transmitter 224, or both. The sensor devices 204, 206, 208, 210, that wirelessly transmit information, and the wireless communication device 200, may be implemented as any form of wireless communication system, such as for proximity wireless communications, vicinity wireless communications, and more distant wireless communications, and other types of wireless communication arrangements as should be appreciated by those of ordinary skill in the art in view of the present discussion. For example, and not for any limitation, a number of wireless communication standards have been developed for various wireless communication applications that can take advantage of an embodiment of the present invention. Such wireless communication standards as ISO 14443 (proximity) and ISO 15963 (vicinity), for example, can be used in alternative embodiments of the present invention. Also, close proximity wireless communication standards such as ECMA-340 or ECMA-352 standards may use other alternative embodiments of the present invention, In any case, alternative embodiments of the present invention should be very broadly interpreted to include many different wireless communication standards and protocols, as should be obvious to those of ordinary skill in the art in view of the present discussion.

According to one exemplary application, the sensor devices 204, 206, 208, 210, comprise RF ID devices that include sensing capability to sense and monitor the presence of at least one of the sanitizing agent comprising ozone and the ultraviolet radiation energy in the storage volume in the package container 202. In this example, the wireless communication device 220 comprises an RF ID reader 220 that can receive and monitor the information from each of the sensor devices 204, 206, 208, 210, to monitor the detection status of the presence of at least one of the sanitizing agent comprising ozone and the ultraviolet radiation energy in the storage volume in the package container 202.

Additionally, the RF ID reader 220 identifies the particular package container 202 that contains the product and/or object 201, in a manner that is well known to those of ordinary skill in the art in view of the present discussion. In this way, in a package storage system 200 storing a plurality of packages, the individual packages can be both monitored and uniquely identified. A particular package container 202, for example, that does not meet certain criteria for detection of the presence of at least one of the sanitizing agent comprising ozone and the ultraviolet radiation energy in the storage volume in the particular package container 202, can be specifically identified to a user of the package storage system 200. A report of information corresponding to the sensed information that is received by the RF ID reader 220 can be provided to a user via a user interface communicatively coupled with the RF ID reader 220. For example, a display of an information processing system (not shown) can display a report of information identifying a particular package container 202 that has failed to maintain an environment in the storage volume that exposes the product and/or object therein to a desired sanitizing, disinfecting, and/or sterilizing treatment. The user then can take corrective action. For example, any suspect packages that fail to meet certain treatment criteria can be removed from the package storage system 200 to remove potential contamination of stored products and/or objects. Additionally, equipment malfunctions can be affirmatively determined by monitoring the internal environment inside the storage volume in each package container 202 in the package storage system 200. Many other monitoring applications using the storage system 200 should be obvious to those of ordinary skill in the art in view of the present discussion. For example, a failure to detect desired ultraviolet radiation energy in the environment of the storage volume in one or more packages can indicate an operational failure of a particular ultraviolet radiation energy source in the storage system 200. As another example, by monitoring the packages in the storage system 200 a particular package container 202 may be determined to be misplaced in the storage system 200 and consequently not receiving the desired sanitizing, disinfecting, and/or sterilizing treatment. It can be appreciated by those of ordinary skill in the art in view of the present discussion that there are many different applications of the storage system 200 according to alternative embodiments of the present invention.

Figure 3:
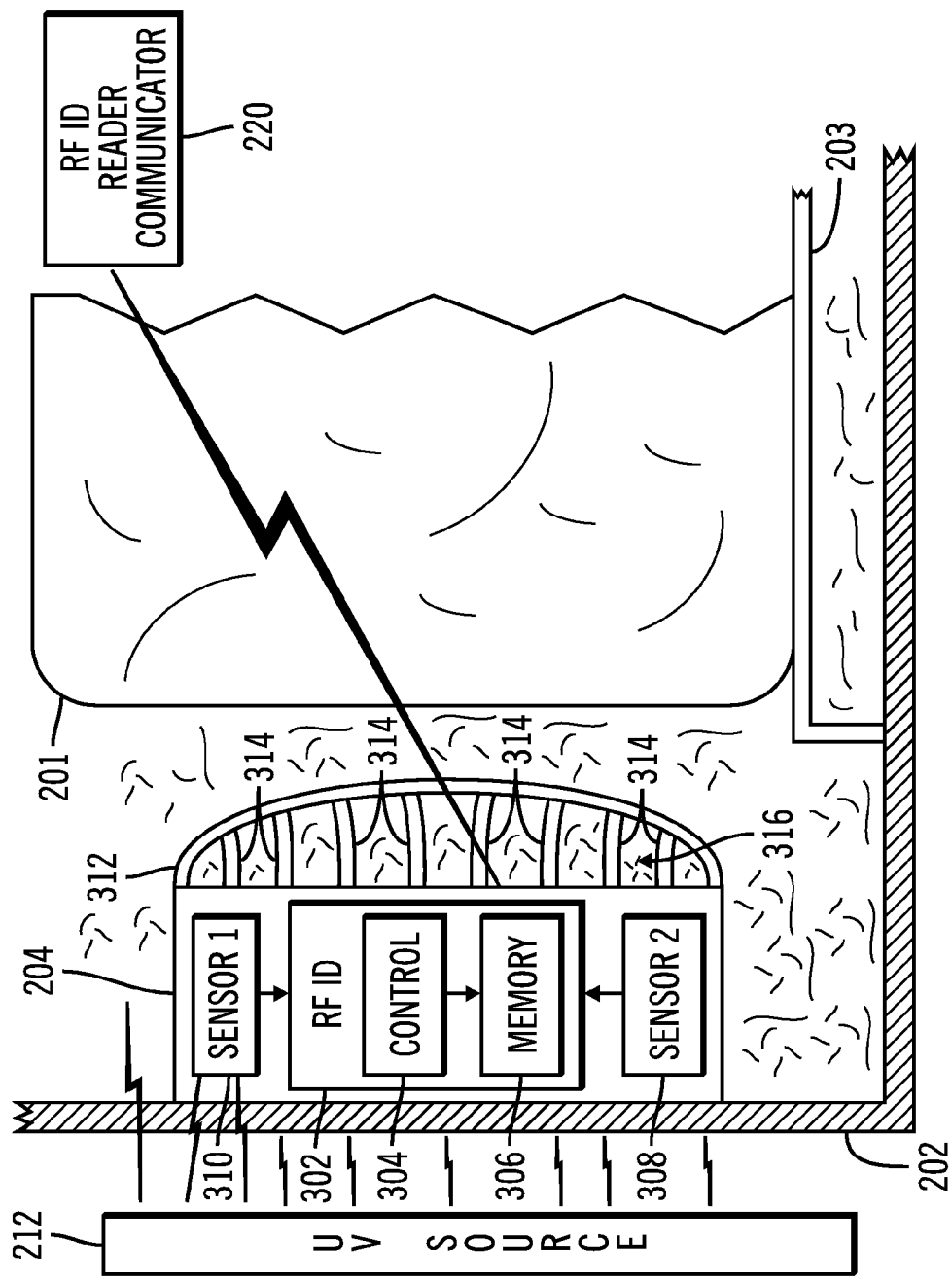
FIG. 3 is a more detailed cross-sectional side view of the packaging system of FIG. 2 focusing on the structure and operation of one sensor device in the packaging system.

Referring now to FIG. 3, a more detailed view of a sensor device 204 in the storage volume of the package container 202 is shown. The sensor device 204, in this example, includes an electronic circuit 302 including a control circuit 304 electrically coupled with a memory circuit that can also implement an RF ID device. The sensor device 204 also includes one or more sensors 308, 310, that are electrically coupled with the electronic circuit 302. As shown in FIG. 3, there are two sensors in the sensor device 204. The first sensor 310 can be used to sense the presence or absence of ultraviolet radiation energy in the storage volume in the package container 202. This ultraviolet radiation energy sensed by the sensor 310 in the storage volume may be at least partially radiated from the ultraviolet radiation source 212 as shown in FIG. 3. The second sensor 318 can be used to sense the presence or absence of ozone gas 316 in the storage volume in the package container 202. This ozone gas 316 sensed by the sensor 308 in the storage volume may be at least partially energizably created in the storage volume by the conversion of a convertible first agent comprising oxygen to a sanitizing agent comprising ozone as a result of the radiation of ultraviolet radiation energy in the storage volume from the ultraviolet radiation source 212 as shown in FIG. 3. The ultraviolet radiation energy at a frequency of about 185 nm will energizably convert the first agent comprising oxygen to a sanitizing agent comprising ozone.

The ultraviolet radiation sensor 310 and the ozone gas sensor 308 can be implemented using modern sensor technology that is similar to semiconductor manufacturing technology and commercially available. Significant advances have been made in sensor technology that can provide silicon micromachined sensors, or microelectromechanical systems sensors. Additionally, modern electrochemical technology has provided many different sensors that may be suitable for use in alternative embodiments of the present invention. A sensor will typically generate an output signal, i.e., a current or voltage signal, in response to sensing the presence of one of the ozone gas or the ultraviolet radiation energy depending on the type of sensor being used. This output signal from the sensors 308, 310, can then be amplified and optionally converted to a usable signal form that is then monitored by the control circuit 304.

The control circuit 304 optionally stores into memory 306 a representation of the sensed information from the sensors 308, 310. The control circuit 304 and the other circuits in the electronic circuit 302 operate to transmit the sensed information (i.e., the representation of the information monitored from the one or more sensors 308, 310) to the wireless receiver (not shown in FIG. 3) of a wireless communication device 220 located outside of the storage volume. In the present example, the sensor device 204 in the storage volume in the package container 202 and the wireless communication device 220 outside of the storage volume communicate according to an RF ID device and wireless reader communication protocol, as is well known to those of ordinary skill in the art in view of the present discussion. That is, the sensor device 204 can operate like an RF ID unit in the storage volume and the wireless communication device 220 outside of the storage volume operates as a wireless RF ID reader 220. The wireless reader 220 can wirelessly communicate with the sensor device and RF ID unit 204 such that the sensed information from one or more of the sensors 308, 310, is wirelessly transmitted from the sensor device 204 in the storage volume in the package container 202 to the wireless reader 220 outside of the storage volume.

Figure 4:
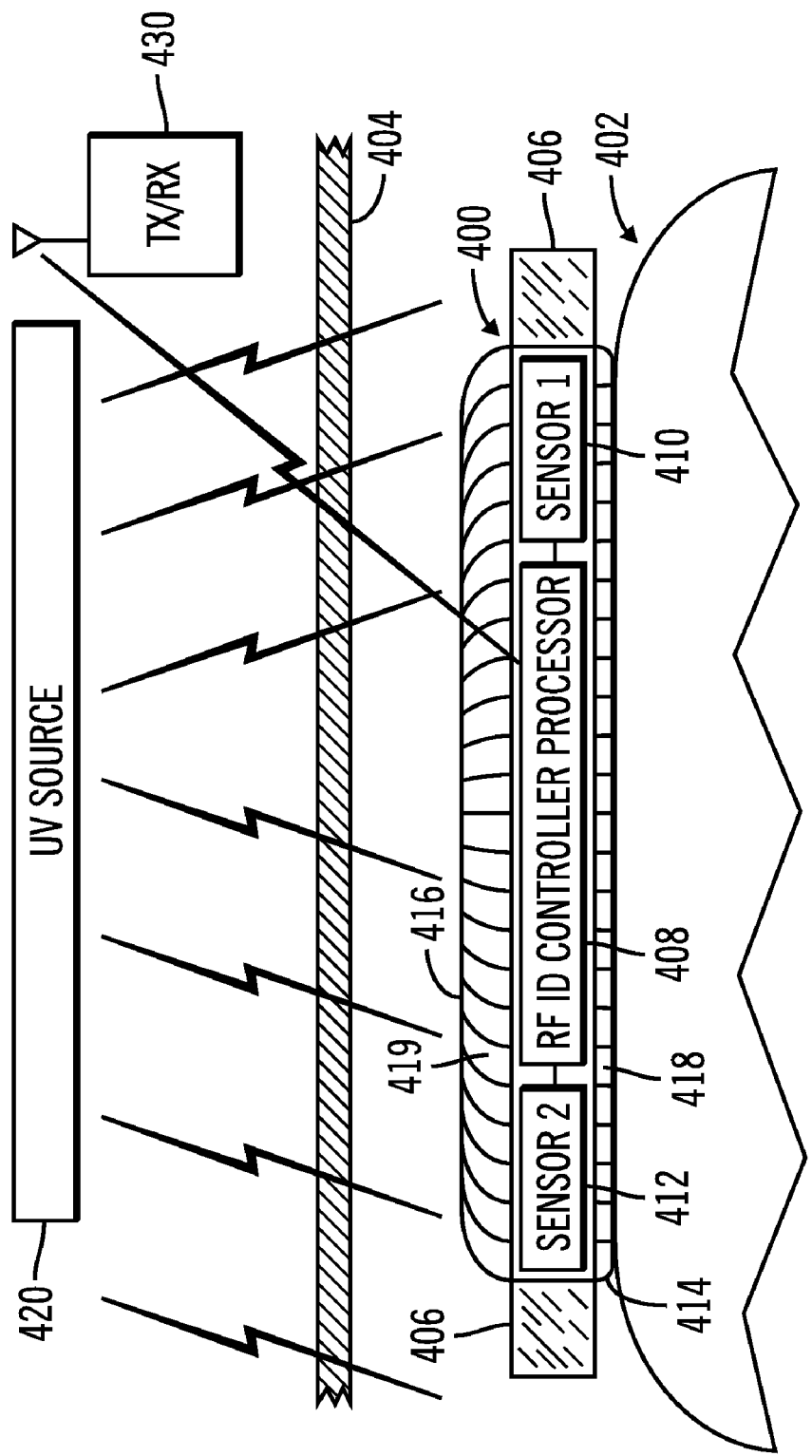
FIG. 4 is a cross-sectional side view of an alternative sensor device arrangement in a packaging system according to an alternative embodiment of the present invention.

Note also in FIG. 3 that an exemplary open space grill cover structure 312 is shown. A series of grill extensions 314 support the cover structure 312 to provide a gap space between the sensor device 204 and an adjacent surface of another object, such as the product or object 201. This gap space allows the presence of the ozone gas 316 to be sensed by the ozone sensor 308. FIG. 4 illustrates a dual gap arrangement for a sensor device 400, according to an embodiment of the present invention. A first open space grill cover 414 and a second open space grill cover 416 provide respective space 418, 419, near the sensor 410, 412, in the sensor device 400. The controller 408 and the sensor 410, 412, can sense and monitor the at least one of a sanitizing agent comprising ozone and ultraviolet radiation energy (such as radiated from the ultraviolet radiation energy source 420) within a gap space 418, 419, on different sides of the sensor device 400. This gap space separates the sensor device 400 from an adjacent surface of a product and/or object 402 in the storage volume of the package container. The controller/processor 408 can then communicate the sensed information to a wireless receiver 430 such as in a wireless reader device 220. In this example, the sensor device 400 is shown as a self-contained sensor device module 400. The sensor device module is freely locatable in the storage volume without direct physical contact restriction to any particular inside surface 404 of the at least one storage volume. This is a different arrangement from the examples of sensor devices 204, 206, 208, 210, shown in FIG. 2 as being mechanically coupled to an inside surface of the storage volume. The coupling, of course, can be direct or indirect between a particular sensor device and an inner surface of a storage volume. It should also be clear that any of the sensor devices 204, 206, 208, 210, according to alternative embodiments of the present invention may be integrally coupled to an inside surface of the at least one storage volume. In such an embodiment, a sensor device 204 may be integral with the package structure and package material at a surface thereof. This allows in certain applications the package structure to incorporate one or more sensor devices 204, 206, 208, 210, ready to be used in a package storage system.

The sensor device module 400, as shown in FIG. 4, includes a substrate 406, a control circuit 408 disposed on the substrate, and at least one sensor 410, 412, mechanically coupled to the substrate 406 and electrically coupled to the control circuit 408, for locating the at least one sensor 410, 412, in the packaging container comprising a storage volume for receiving products and/or objects therein. The at least one sensor 410, 412, monitors the presence of at least one of the sanitizing agent comprising ozone and ultraviolet radiation energy in the storage volume of the packaging container.

Figure 5:
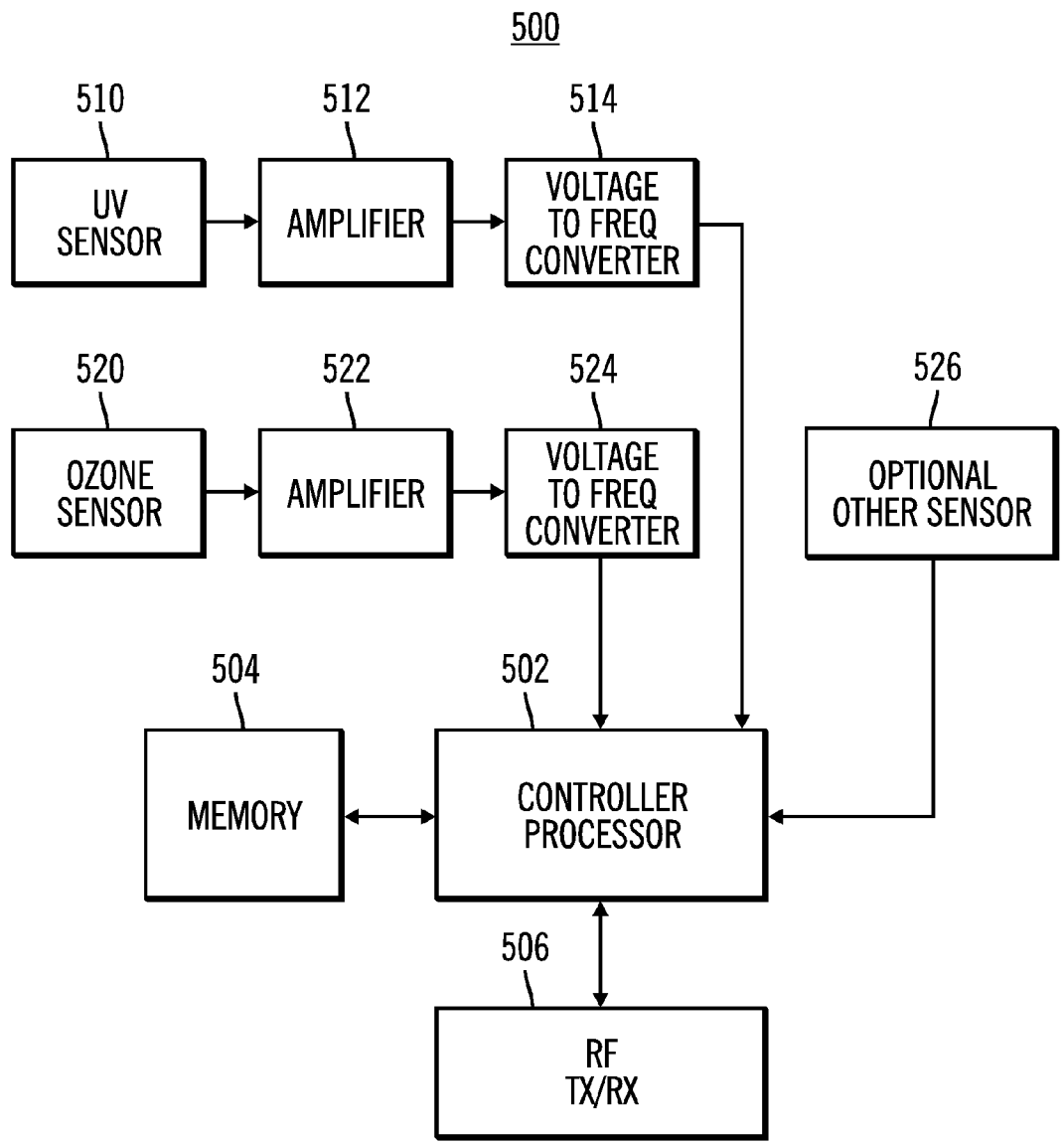
FIG. 5 is an electrical block diagram illustrating an exemplary sensor device arrangement for use in a packaging system according to an embodiment of the present invention.

The structure and function of components in an exemplary sensor device 500 are shown in FIG. 5. FIG. 5 illustrates an exemplary circuit arrangement accommodating a plurality of sensors in a sensor device 500. In this example, an output signal from an ultraviolet radiation sensor 510, indicative of the presence of ultraviolet radiation energy at the sensor 510, is amplified by an amplifier circuit 512 which then provides the amplified signal to a voltage to frequency converter 514. The output from the voltage to frequency converter 514 can be monitored by the controller/processor circuit 502. The ozone sensor 520 monitors the presence of ozone gas at the ozone sensor 520 and provides an output signal that is amplified by an amplifier circuit 522 which then provides the amplified signal to a voltage to frequency converter 524. The output from the voltage to frequency converter 524 can be monitored by the controller/processor circuit 502. The controller/processor 502 can also store in memory 504 information corresponding to the sensor information to represent the sensed presence, or lack thereof, of the ultraviolet radiation energy at the ultraviolet radiation sensor 510 and the sensed presence, or lack thereof, of the ozone gas at the ozone sensor 520.

Other sensors 526 can optionally be monitored by the controller/processor 502 in the sensor device 500. For example, other sensors such as a temperature sensor, a relative humidity sensor, a gas sensor for sensing a gas other than ozone, an accelerometer sensor that senses movement of the sensor device 500 and accordingly indicates movement of a package container that contains the sensor device 500, and other types of sensors for various applications for use with products and/or objects to be packaged as should be obvious to those of ordinary skill in the art in view of the present discussion. In particular, note that an accelerometer or other type of motion sensor in the sensor device 500 allows a package storage system to wirelessly monitor the movement and rotation of the product and/or object in the storage volume of the package container 202. This can also be used to indicate whether the rotational motion of the product and/or object in the storage volume of the package container 202 will be sufficient to expose different surfaces of the product and/or object to a sanitizing, disinfecting, and/or sterilizing treatment while in the package container 202. Such information can be very useful for a package storage system 200 to make sure that products and/or objects in packages stored in a package storage system 200 are receiving the desired treatment.

Lastly, as shown in FIG. 5, a wireless transmitter and receiver circuit 506 is electrically coupled to the controller/processor 502. The sensor device 500 can wirelessly transmit sensed information to a wireless receiver 222 outside of the storage volume of a package container 202. The wireless receiver 222 provides the received sensed information to a controller/processor, such as at a wireless reader device 220, that monitors the presence of the at least one of the ultraviolet radiation energy and the ozone gas 316 in the storage volume of the package container 202. Optionally, the wireless reader device 220 includes a wireless transmitter circuit 224 and the sensor device 500 includes a wireless receiver circuit 506. Information can be transmitted from the reader device 220 to the sensor device 500 in the storage volume. Such received information at the sensor device 506 can be used by the controller/processor 502 to do any of the following: configure parameters and change the operation of the sensor device 500, to adjust the operation of the different sensors 510, 520, 526, in the sensor device 500, to optionally change a program and/or data in the sensor device 500, or any other adjustment or configuration of the sensor device 500 and its components as should be obvious to those of ordinary skill in the art in view of the present discussion. The communication with the sensor device 500 can be effected during use in the storage volume in the package container 202, allowing much flexibility in changing the operation of the sensor device 500 even while in use.

Figure 6:
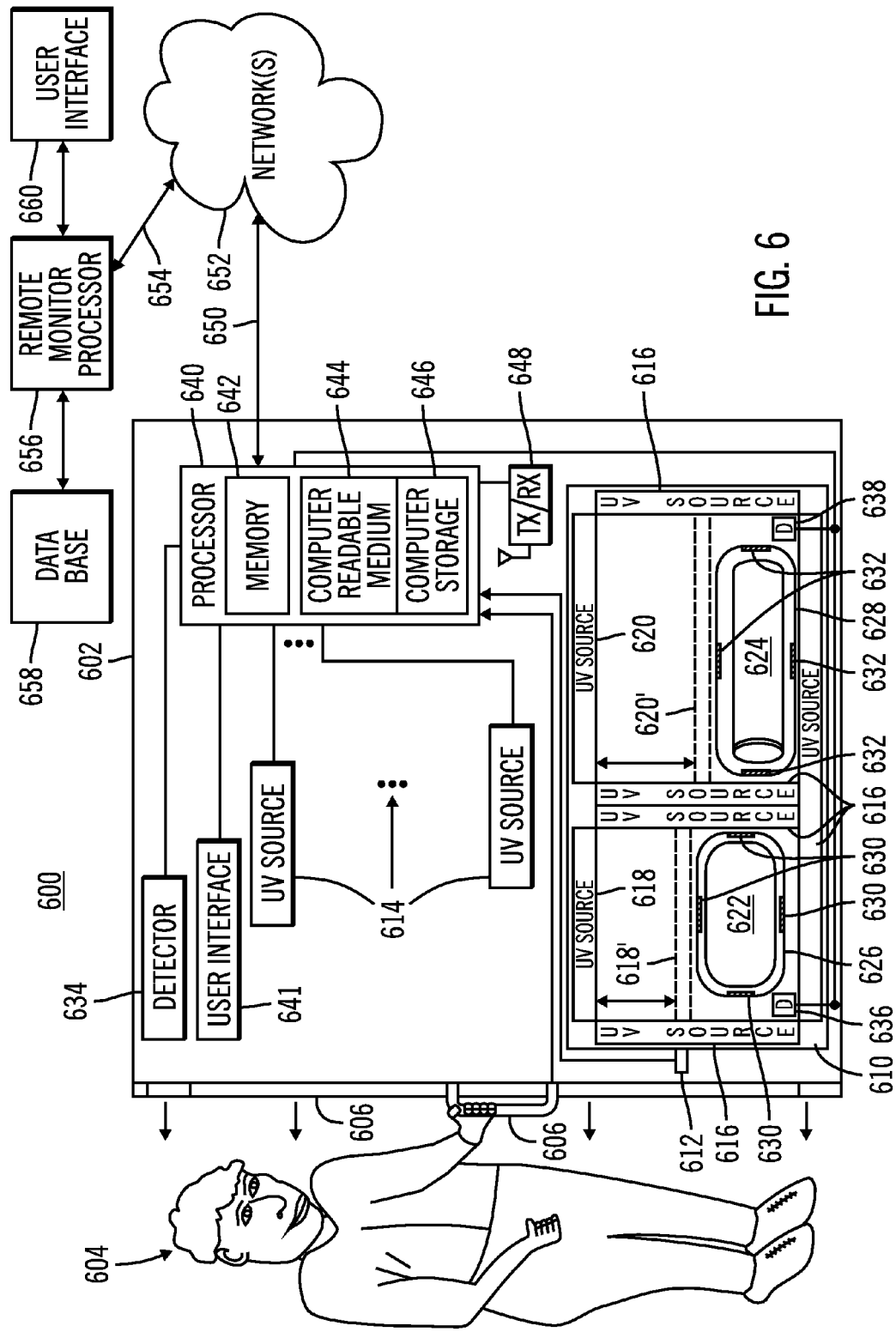
FIG. 6 is a diagram illustrating an exemplary control and monitoring system for a package storage system, in accordance with an embodiment of the present invention.

Referring to FIG. 6, an alternative embodiment for a package storage system 600 is shown. A package storage unit 602 can be any type of storage for containing packaged and unpackaged products and/or objects. For example, the package storage unit 602 may comprise any combination of a refrigerated locker, a storage locker, a storage room or warehouse area, a moving carrier storage area, or the like. Various ultraviolet radiation energy sources 614, 616, 618, 620, can be energized at a first frequency of ultraviolet radiation, such as about 253 nm wavelength range, such as for providing a strong anti-microbial killing effect on all surfaces, including the surfaces of products and/or objects 622, 624, being packaged 626, 628, and stored, respectively, in one or more storage volumes in the package storage unit 602. Alternatively, the various ultraviolet radiation energy sources 614, 616, 618, 620, can be energized at a second ultraviolet radiation energy frequency, such as about 185 nm wavelength range, to convert the convertible agent comprising oxygen in the one or more storage volumes to the sanitizing agent comprising ozone. The sanitizing agent comprising ozone provides additional sanitizing and/or sterilizing effect to the products and/or objects 622, 624, being packaged and stored in the one or more storage volumes in the package storage unit 602.

The products and/or objects 622, 624, sealed in the respective package containers 626, 628, will be protected from external hazards and contaminants while still receiving, as desired, the ultraviolet energy radiation energy to alternatively provide the strong anti-microbial killing effect of the ultraviolet radiation energy at a first frequency, such as about 253 nm wavelength range, and to provide the additional sanitizing and/or sterilizing effect of the sanitizing agent comprising ozone being energizeably converted from the convertible agent comprising oxygen while being exposed to the ultraviolet radiation energy at the second frequency, such as at about 185 nm wavelength range. The contained products and/or objects 622, 624, being sanitized and/or sterilized remain protected from outside contaminants while in the respective packages 626, 628.

Product storage can take many forms. For example, a freezer or refrigeration system can store product within shelves or storage bins to great lengths of time before consumption or use of the products and/or objects. As illustrated in FIG. 6, the products and/or objects 622, 624, are stored in a storage drawer 610 contained within the package storage unit 602. In this example, only as an example and not for any limitation in the broad scope of the alternative embodiments of the present invention, the package storage unit 602 comprises a refrigerated storage unit or a refrigerator.

A user 604 can request to open the package storage unit 602 via a sensor at the handle 608 of the door 606. The door will be controlled by the controller/processor 640 to maintain the door closed until the environment inside the package storage unit 602 is safe for the user's 604 access. For example, the controller/processor 640 maintains the door 606 locked until both the ozone has been substantially converted back to oxygen inside the package storage unit 602 and all of the ultraviolet radiation sources 614, 616, 618, 620, have been turned OFF. At least one ozone detector 634 inside a main compartment of the package storage unit 602 can affirmatively detect the presence of ozone therein and provide the sensed and detected information to the controller/processor 640.

User access to the storage drawer 610, according to an embodiment, is separately controllable by the controller/processor 640. A sensor at the handle 612 of the storage drawer 610 will detect when the user 604 is requesting access to the inside of the storage drawer 610. The controller/processor 640 can control the ultraviolet radiation energy sources 616, 618, 620, in the storage drawer 610 to convert ozone to oxygen thereby substantially reducing any ozone gas present in the storage drawer 610 before the user is allowed access inside. One or more ozone detectors 636, 638, can sense the presence of ozone in the environment inside one or more storage volumes in the storage drawer 610. Also, of course, the ultraviolet radiation energy sources 616, 618, 620, inside of the storage drawer 610 are turned OFF before the user is allowed access inside. According to one embodiment, the controller/processor 640 can allow user access to the main compartment of the package storage unit 602, while preventing access to the storage drawer 610 while continually provide a sanitizing, disinfecting, and/or sterilizing, treatment to the products and/or objects 622, 624, in packages 626, 628, stored in the storage drawer compartment 610. The storage drawer 610 can be accessed by the user after the processor 640 determines that the environment in the storage volumes in the storage drawer 610 is safe for user access, such as when there is no ozone detected and the ultraviolet radiation energy sources 616, 618, 620, in the storage drawer 610 are all turned OFF.

Each package container 626, 628, includes respectively one or more sensor devices 630, 632, inside a storage volume of the package container 626, 628. These sensor devices 630, 632, as have been discussed above, can monitor the presence of at least one of a sanitizing agent comprising ozone and ultraviolet radiation energy in the storage volume of the package container 626, 628. The sensor devices 630, 632, can also wirelessly communicate with wireless receiver and transmitter circuits 648 communicatively coupled with the processor 640. In this way, the processor 640 can monitor the presence of at least one of a sanitizing agent comprising ozone and ultraviolet radiation energy in the storage volume of the package container 626, 628. The processor 640 stores in memory 642 the sensed information from the sensor devices 630, 632. Additionally, the processor can identify each package container 626, 628, such as by using RF ID wireless communication technology and protocol. In this way, a package 626, 628, that fails to meet certain criteria with respect to a sanitizing, disinfecting, and/or sterilizing, treatment can be specifically identified and corrective action may be taken. The processor 640, in this example, includes computer storage, such as hard disk drive unit 646 for maintaining a data repository, such as a database, to track the monitoring process of the packages being stored in the package storage unit 602. Additionally, a computer readable medium 644 can be used to transfer information, such as program and data, to/from the processor 640.

A user interface 641 at the package storage unit 602 can provide information to, and receive commands and data from, the user 604. For example, a display at the user interface 641 can report information to the user to identify a status of treatment for product and/or object stored in a particular package 626, 628. A keyboard at the user interface 641 can accept user input from the user 604, such as to input commands to the processor 640 to adjust the operation of the processor 640, or to adjust the operation of one or more of the sensor devices 630, 632, inside the packages 626, 628, stored in the package storage unit 602.

In the package storage unit 602, according to the present example, there are stationary ultraviolet radiation sources 614, 616, and there are movable ultraviolet radiation sources 618, 618', and 620, 620'. These ultraviolet radiation sources are movable, in one embodiment, manually by a user 604, such as part of an operation of adding or removing packages 626, 628, that are contained in the storage drawer 610. The movable ultraviolet radiation sources 618, 620, in an alternative embodiment, can be automatically movable under control from the processor 640. A controllable moving mechanism and guide under control from the processor 640 can move the movable ultraviolet radiation sources 618, 618', and 620, 620', to adjust the distance between the movable ultraviolet radiation sources 618, 618', and 620, 620', and the packages 626, 628, contained in the respective storage volumes in the storage drawer 610. The closer the movable ultraviolet radiation sources 618, 618', and 620, 620', are to the respective packages 626, 628, the more ultraviolet radiation energy from these sources 618, 620, will be delivered into the storage volumes in the packages 626, 628. This movement and adjustment of distance can significantly enhance the sanitizing, disinfecting, and/or sterilizing, treatment applied to the products and/or objects 622, 624, contained in the packages 626, 628.

The processor 640, according to an alternative embodiment, can communicate the sensed information received from the wireless receiver circuit 648 to a remote processor 656. The communication with the remote processor 656 can be over one or more communication links 650, 654, and over one or more networks 652, in a manner that is well known to those of ordinary skill in the art. The communication links and networks 652 may include wide area networks, local area networks, wireless communication networks, and satellite communication networks, and other networks as should be obvious to those of ordinary skill in the art. In this way, the sensed information from the sensor devices 630, 632, can be communicatively coupled to the processor 640 at the package storage unit 602 for local monitoring by the user 604. Additionally, it can also be communicatively coupled to the processor 656 that may be located remotely at a central location to remotely monitor the treatment status of the products and/or objects 622, 624, being contained in packages 626, 628, and stored in the one or more storage volumes in the package storage unit 602.

The remote processor 656 can be coupled with a data repository 658, such as a database, that can store, among other things, the sensed information received from the sensor devices 630, 632, the identification of the particular packages 626, 628, the identification of the package storage unit 602, the identification of the responsible user 604, time/date information, the history of storage for each of the packages 626, 628, that have been stored over time at one or more storage units and storage locations, and other such information associated with the package storage system 600 to monitor and track the operation and use of the package storage system 600. In particular, the stored information at the data repository 658 can be provided to a user via a user interface 660. This stored information at the data repository 658 allows the user at a remote location to monitor the sensed information from the sensor devices 630, 632, as well as all other collected and tracked information, as discussed above, to thereby monitor the treatment status of the products and/or objects 622, 624, contained in the packages 626, 628, stored in the package storage unit 602. Additionally, an analysis of any package 626, 628, and/or the product and/or object 622, 624, presently contained therein, can trace the treatment history of such package 626, 628, and/or such product and/or object 622, 624. This allows a significant advantage in quality control and monitoring such as to track freshness and sanitary handling for packaged products and/or objects being processed in a package storage system 600.

Figure 7:
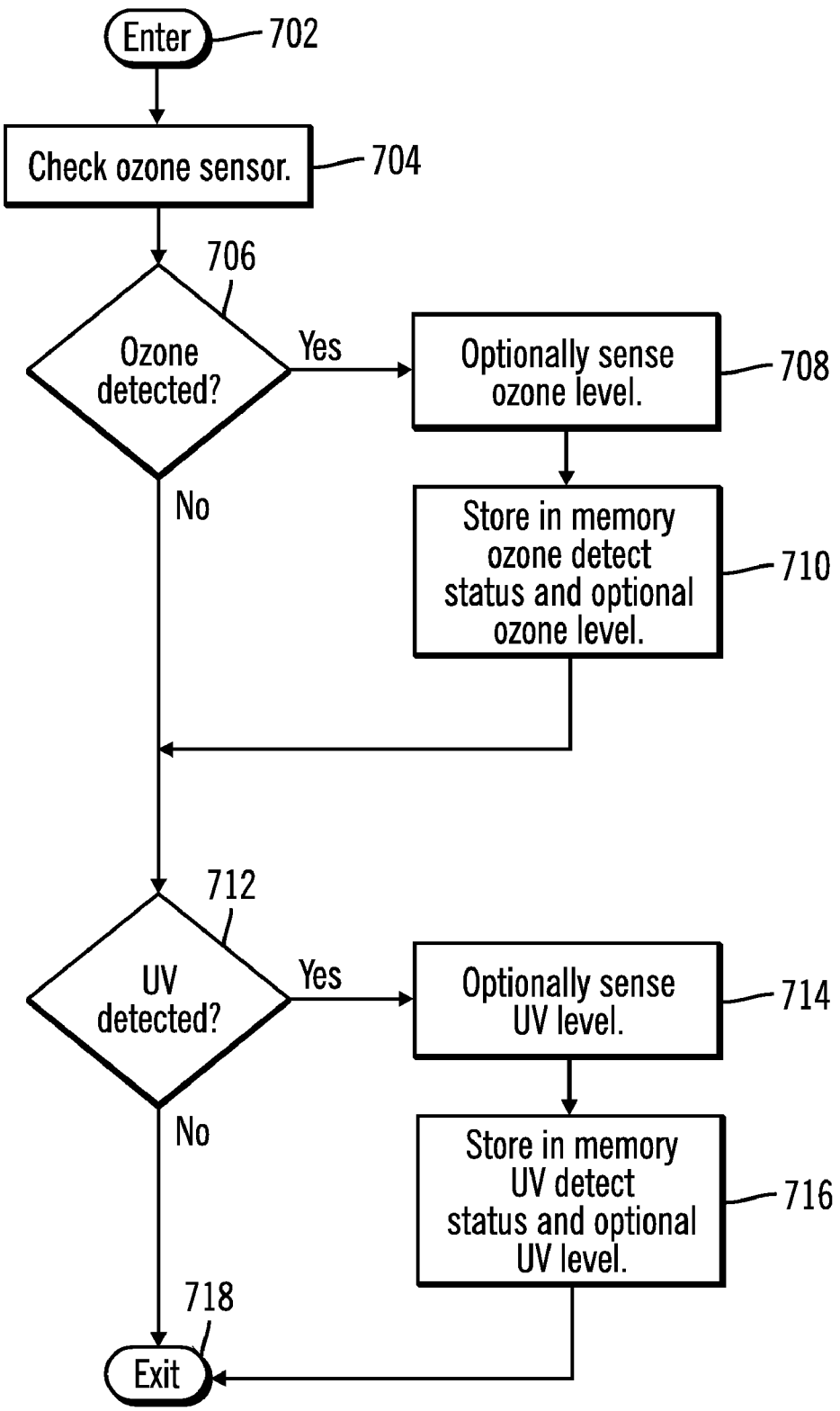
FIGS. 7-9 are operational flow diagrams illustrating exemplary operational flow sequences for the control and monitoring system for the package storage system shown in FIG. 6, according to embodiments of the present invention.
Figure 8:
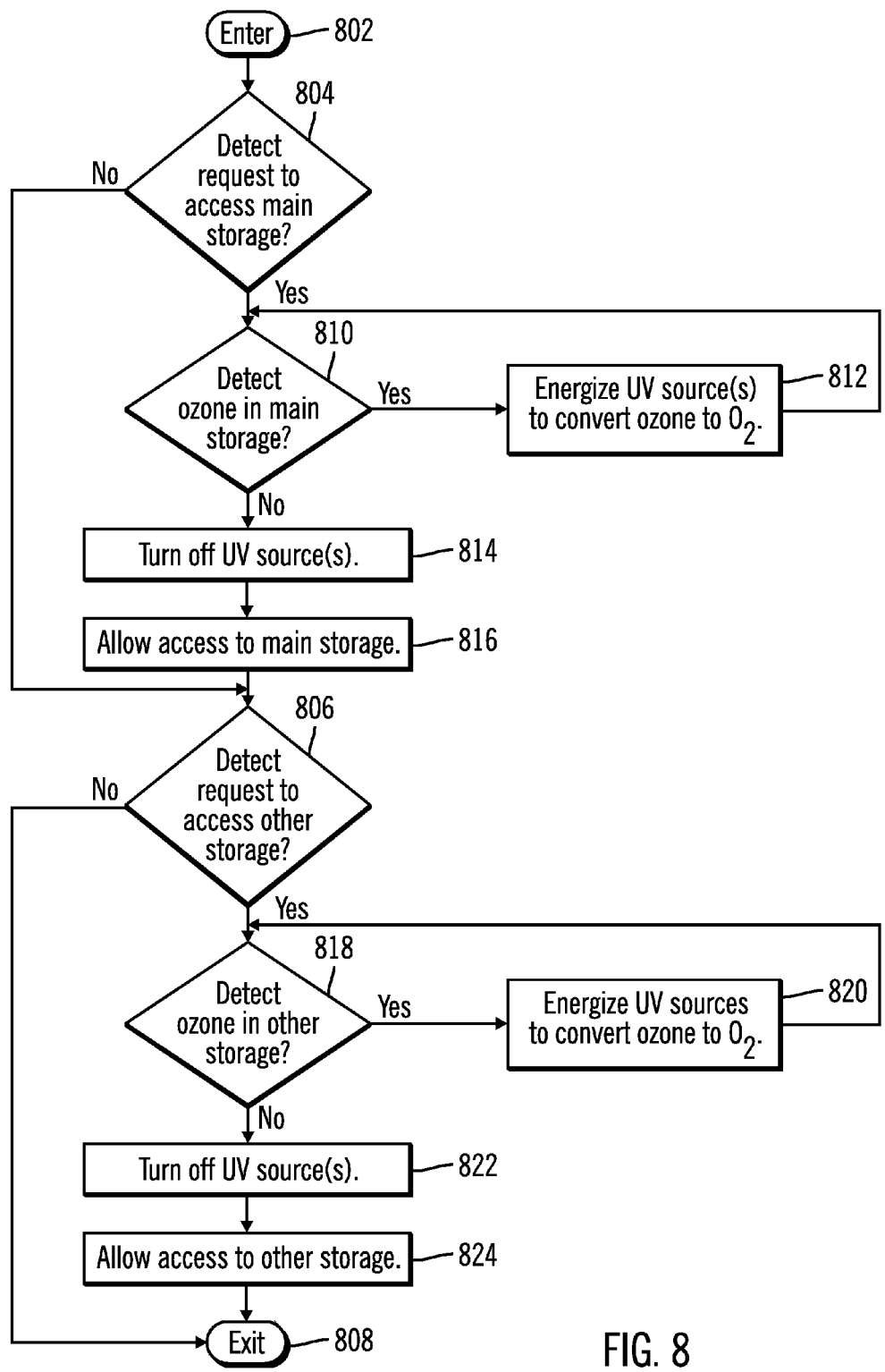
Figure 9:
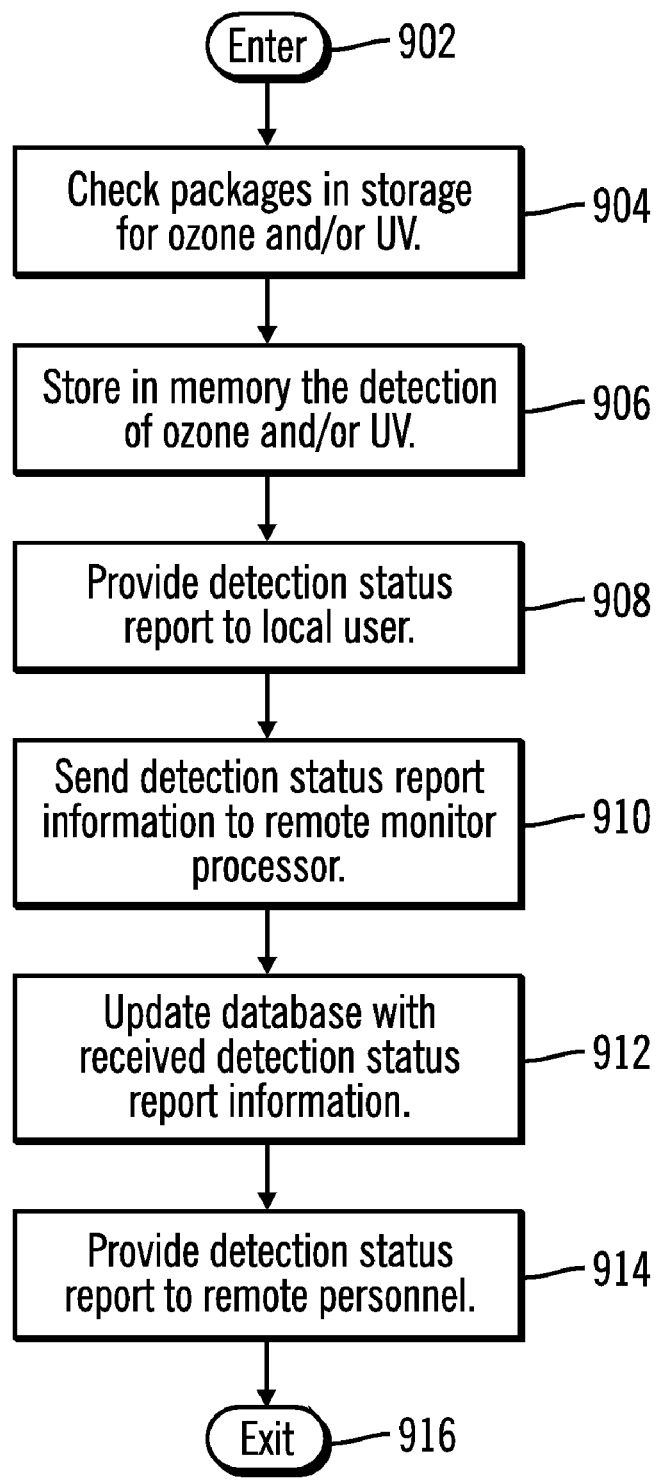

FIGS. 7 through 9 illustrate various exemplary operational flow sequences for a package storage system 600, such as shown in FIG. 6. FIG. 7 illustrates an operational flow sequence at a sensor device 630, 632. The sensor device 630, 632, in this example, is represented by the sensor device 500 shown in FIG. 5, which includes an ozone sensor 520 and an ultraviolet radiation energy sensor 510. The processor 502, checks the ozone sensor 520, at step 704. If ozone is not detected, at step 706, the processor 502 goes to check whether there us ultraviolet radiation energy detected. If no ultraviolet radiation energy is detected, at step 712, then the processor 502 of the sensor device 500 exits the operational flow sequence, at step 718. This checking for detection of ozone gas and for detection of ultraviolet radiation energy can be done at predetermined time intervals or repeated continuously. If ozone gas is detected by the ozone sensor 520, at step 706, the controller 502 can optionally check the sensor output to try to determine at least an estimate of the level of ozone that is detected, at step 708. The controller 502 then stores this sensed information in memory 504, at step 710. If ultraviolet radiation energy is detected by the ultraviolet radiation energy sensor 510, at step 712, the controller 502 can optionally check the sensor output to try to determine at least an estimate of the level of ultraviolet radiation energy, at step 714. Optionally, in an embodiment of the present invention, multiple ultraviolet radiation energy sensors in the sensor device 500 can each detect generally a frequency range of ultraviolet radiation energy, such as one sensor for detecting about 253 nm frequency range and a second sensor for detecting about 185 nm frequency range. In such an arrangement for a sensor device 500, the controller 502 can detect the presence of ultraviolet radiation energy and at a particular frequency range, such as at about 253 nm and about 185 nm. The controller 502 then stores this sensed information in memory 504, at step 716.

With reference to FIG. 8, the operational flow sequence shown illustrates the package storage unit 600 independently controlling user access to the main storage compartment, such as via the door handle 608 and associated sensor, and user access to the storage drawer compartment 610, such as via the drawer handle 612 and associated sensor. The processor 640 monitors the sensors associated with the handles 608, 612, and the processor 640 determines whether a user is requesting access to either the main storage compartment or the storage drawer compartment 610. If the processor 640 determines that no user request is detected then the operational flow sequence exits, at steps 802, 804, 806, 808.

If a user request to access the main storage compartment is detected, at step 804, the controller/processor 640, checks, at step 810, whether ozone is detected in the main compartment. If it is detected, then the controller 640 controls the controllable ultraviolet radiation energy sources 614 in the main storage compartment to convert ozone to oxygen, at step 812. When no more ozone is detected in the main storage compartment, at step 810, the controller 640, turns OFF all ultraviolet radiation energy sources 614, at step 814, and allows user access to the main storage compartment, at step 816. Note that, in this example, while the user accesses the main storage compartment, the ultraviolet radiation energy sources 616, 618, 620, in the storage drawer compartment 610 can be operational and ozone gas may be present in the storage volumes in the storage drawer compartment 610. That is, the storage drawer compartment 610 remains gas tight sealed to prevent ozone from escaping into the main storage compartment and the outer structure of the storage drawer compartment 610 is substantially opaque to ultraviolet radiation energy thereby blocking the ultraviolet radiation energy from exiting the storage drawer compartment 610 into the main storage compartment. In this way, a sanitizing, disinfecting, and/or sterilizing treatment can be continuously applied to the products and/or objects 622, 624, contained in the storage drawer compartment 610, even while the user 604 accesses the main storage compartment.

Then, if the controller/processor 640 detects a user request to access the storage drawer compartment 610, at step 806, the processor 640 determines whether ozone is detected in the storage drawer compartment 610; and energizes the ultraviolet radiation energy sources 616, 618, 620, in the storage drawer compartment 610 to convert ozone to oxygen, at steps 818, 820. When no more ozone is detected in the storage drawer compartment, at step 818, the controller 640, turns OFF all ultraviolet radiation energy sources 616, 618, 620, at step 822, and allows user access to the main storage compartment, at step 824, and exits the operational flow sequence, at step 808.

Referring to FIG. 9, an exemplary operational flow sequence illustrates monitoring and tracking of sensed information from the sensor devices 630, 632, to monitor the status of sensing in the storage volumes of the packages 626, 628, the presence of at least one of a sanitizing agent comprising ozone and ultraviolet radiation energy.

The processor 640 wirelessly communicates, at step 902, 904, with the sensor devices 630, 632, in the storage volumes in the packages 626, 628, to receive sensed information from the sensor devices 630, 632. The controller 640 monitors the status of detection of the presence of at least one of ozone and ultraviolet radiation energy in the storage volume of each of the packages 626, 628. Then, at step 906, the controller 640 stores the received sensed information in memory 642, such as in a local data repository or database. The processor 640, at step 908, communicates via the local user interface 641 with the user 604 to provide to the user 604 the sensed information and/or a status of detection of the presence of at least one of ozone and ultraviolet radiation energy in the storage volume of each of the packages 626, 628.

The processor 640, at step 910, communicatively couples the sensed information and/or the detection status information to the remote processor 656. The remote processor 656, at step 912, updates the data repository 658, or database, with the received information from the processor 640 of the package storage unit 602. Additionally, the remote processor 656, at step 914, provides to a user via the user interface 660 the received information from the processor 640 of the package storage unit 602. In this way, the remotely located user can remotely monitor the received sensed information from the sensor devices 630, 632, and/or the status of detection of the presence of at least one of ozone and ultraviolet radiation energy in the storage volume of each of the packages 626, 628. This remote monitoring by the remote processor 656 and by a remotely located user, as well as the monitoring by the processor 640 and the user 604 at the package storage unit 602, is a significant advantage of an embodiment of the present invention. The ability to monitor and manage the quality control and freshness and sanitary conditions of packaged products and/or goods that can be remotely located to a monitoring station, provides many benefits to a package storage system enhancing the commercial viability of a package storage related business, a package distribution related business, and/or any business that has a need for improving its management, storage, and distribution of packaged products.

The present invention can be realized in hardware, software, or a combination of hardware and software. A system according to an exemplary embodiment of the present invention can be realized in a centralized fashion in one computer system, or in a distributed fashion where different elements are spread across several interconnected computer systems. Any kind of computer system—or other apparatus adapted for carrying out the methods described herein—is suited. A typical combination of hardware and software could be a general purpose computer system with a computer program that, when being loaded and executed, controls the computer system such that it carries out the methods described herein.

The present invention can also be embedded in a computer program product, which comprises all the features enabling the implementation of the methods described herein, and which—when loaded in a computer system—is able to carry out these methods. Computer program means or computer program in the present context mean any expression, in any language, code or notation, of a set of instructions intended to cause a system having an information processing capability to perform a particular function either directly or after either or both of the following a) conversion to another language, code or, notation; and b) reproduction in a different material form.

Each computer system may include, inter alia, one or more computers and at least one computer readable medium that allows a computer to read data, instructions, messages or message packets, and other computer readable information. The computer readable medium may include non-volatile memory, such as ROM, Flash memory, Disk drive memory, CD-ROM, and other permanent storage. Additionally, a computer medium may include, for example, volatile storage such as RAM, buffers, cache memory, and network circuits. Furthermore, the computer readable medium may comprise computer readable information in a transitory state medium such as a network link and/or a network interface, including a wired network or a wireless network, that allow a computer to read such computer readable information.

Although specific embodiments of the invention have been disclosed, it will be understood by those having ordinary skill in the art that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A self-monitoring package arrangement comprising:
    a packaging container for receiving one or more products and/or objects therein, the packaging container having a packaging structure comprising packaging material providing at least one storage volume, the at least one storage volume for containing a first agent that is energizably convertible by an energy source to a sanitizing agent comprising ozone in the at least one storage volume, the sanitizing agent comprising ozone being transferable from the at least one storage volume to the one or more products and/or objects to provide at least one of a sanitizing, disinfecting, and sterilizing, application to the one or more products and/or objects; and
    at least one sensor device, being located in the at least one storage volume, with one or more of the at least one sensor device each comprising an ultraviolet radiation sensor located in close proximity to an inside surface of the packaging material of the packaging structure providing the at least one storage volume of the packaging container and the ultraviolet radiation sensor being oriented substantially toward the nearest inside surface of the packaging material of the packaging structure providing the at least one storage volume to detect ultraviolet radiation energy radiated through the packaging material and into the at least one storage volume, to monitor the presence of at least one of the sanitizing agent comprising ozone and ultraviolet radiation energy in the at least one storage volume thereby monitoring exposure of the products and/or objects being stored in the at least one storage volume to the at least one of the sanitizing agent comprising ozone and the ultraviolet radiation energy.

2. The self-monitoring package arrangement of claim 1, wherein the ultraviolet radiation energy in the at least one storage volume comprising ultraviolet radiation energy being radiated in the at least one storage volume by an ultraviolet radiation energy source located outside of the at least one storage volume, the at least one sensor device being mechanically coupled to the inside surface and the at least one sensor device comprising an ultraviolet radiation sensor oriented in the at least one storage volume substantially toward the nearest inside surface of the packaging material of the at least one storage volume to detect ultraviolet radiation energy radiated through the packaging material and into the at least one storage volume, to monitor the presence in the at least one storage volume of the at least one of
the sanitizing agent comprising ozone, and
the ultraviolet radiation energy from the ultraviolet radiation energy source located outside of the at least one storage volume.

3. The self-monitoring package arrangement of claim 1, wherein the at least one sensor device being mechanically coupled to an inside surface of the at least one storage volume.

4. The self-monitoring package arrangement of claim 1, wherein the at least one sensor device being incorporated in the packaging material and packaging structure of the packaging container and thereby integrally coupled to an inside surface of the at least one storage volume.

5. The self-monitoring package arrangement of claim 1, wherein the at least one sensor device comprising a sensor device module including:
a substrate; and
at least one sensor mechanically coupled to the substrate, the at least one sensor for monitoring the presence of the at least one of the sanitizing agent comprising ozone and the ultraviolet radiation energy in the at least one storage volume; and wherein:
the sensor device module being unattached to any inside surface of the packaging material of the packaging structure providing the at least one storage volume, in unrestricted location inside the at least one storage volume and thereby freely locatable in the at least one storage volume without direct physical contact restriction to any particular inside surface of the at least one storage volume.

6. The self-monitoring package arrangement of claim 1, wherein the energy source is located outside of the packaging container, and wherein the first agent comprises oxygen and the first agent is energizably convertible to the sanitizing agent comprising ozone by ultraviolet radiation energy including ultraviolet radiation energy at about a 185 nanometer wavelength range radiated from the energy source and through the packaging material and into the at least one storage volume at a first state of the energy source, and wherein the sanitizing agent comprising ozone is energizably convertible to the first agent comprising oxygen by ultraviolet radiation energy including ultraviolet radiation energy at about a 253 nanometer wavelength range radiated from the energy source and through the packaging material and into the at least one storage volume at a second state of the energy source, and wherein the at least one sensor device including a plurality of sensors for monitoring the presence of a respective plurality of the sanitizing agent comprising ozone, the ultraviolet radiation energy including ultraviolet radiation energy at about a 185 nanometer wavelength range radiated from the energy source at the first state of the energy source, and the ultraviolet radiation energy including ultraviolet radiation energy at about a 253 nanometer wavelength range radiated from the energy source at the second state of the energy source, in the at least one storage volume.

7. The self-monitoring package arrangement of claim 1, comprising at least one energy source located outside of the packaging container, and wherein the at least one energy source comprises
a first ultraviolet radiation energy source to radiate a first ultraviolet radiation energy including ultraviolet radiation energy at about a 185 nanometer wavelength range radiated from the first ultraviolet radiation energy source through the packaging material and into the at least one storage volume to energizably convert the first agent comprising oxygen to the sanitizing agent comprising ozone in the at least one storage volume; and
a second ultraviolet radiation energy source to radiate a second ultraviolet radiation energy that delivers antimicrobial ultraviolet energy through the packaging material and into the at least one storage volume and to exposed surfaces of the one or more products and/or objects being stored in one of the at least one storage volume, the at least one sensor device for monitoring the presence of at least one of the sanitizing agent comprising ozone, the first ultraviolet radiation energy, and the second ultraviolet radiation energy, in the at least one storage volume.

8. The self-monitoring package arrangement of claim 7, wherein the first ultraviolet radiation energy source radiates through the packaging material and into the at least one storage volume first ultraviolet radiation energy including ultraviolet radiation energy at about a 185 nanometer wavelength range, and wherein the second ultraviolet radiation energy source radiates through the packaging material and into the at least one storage volume second ultraviolet radiation energy including ultraviolet radiation energy at about a 253 nanometer wavelength range.

9. The self-monitoring package arrangement of claim 1, wherein the at least one sensor device comprises an RF ID device being wirelessly readable from a wireless reader device located outside of the at least one storage volume, to monitor the presence of at least one of the sanitizing agent comprising ozone and the ultraviolet radiation energy in the at least one storage volume by the wireless reader device thereby monitoring, outside of the at least one storage volume, the exposure of the one or more products and/or objects being stored inside of the at least one storage volume to the at least one of the sanitizing agent comprising ozone and the ultraviolet radiation energy, and further wherein the RF ID device of the at least one sensor device being wirelessly readable from the wireless reader device to uniquely identify a packaging container, that contains one or more products and/or objects, from other packaging containers.

10. A package storage system, comprising:
a storage container for containing at least one package in a first storage volume of the storage container, the at least one package having a packaging structure comprising packaging material providing at least one storage volume for receiving a product and/or object therein, the at least one storage volume for containing a first agent that is energizably convertible by an energy source to a sanitizing agent comprising ozone in the at least one storage volume, the sanitizing agent comprising ozone being transferable from the at least one storage volume to the product and/or object to provide at least one of a sanitizing, disinfecting, and sterilizing, application to the product and/or object;

at least one sensor device being located in the at least one storage volume of the at least one package, with one or more of the at least one sensor device each comprising an ultraviolet radiation sensor located in close proximity to an inside surface of the packaging material of the packaging structure providing the at least one storage volume of the at least one package and the ultraviolet radiation sensor being oriented substantially toward the nearest inside surface of the packaging material of the packaging structure providing the at least one storage volume to detect ultraviolet radiation energy radiated through the packaging material and into the at least one storage volume, to monitor the presence of at least one of the sanitizing agent comprising ozone and ultraviolet radiation energy in the at least one storage volume thereby monitoring exposure of the product and/or object being stored in the at least one storage volume to the at least one of the sanitizing agent comprising ozone and the ultraviolet radiation energy;

at least one ultraviolet radiation energy source in the storage container, the at least one ultraviolet radiation energy source being energizable to provide ultraviolet radiation energy in the at least one storage volume of the at least one package for energizably converting the first agent to a sanitizing agent comprising ozone in the at least one storage volume to provide at least one of a sanitizing, disinfecting, and sterilizing, application to the product and/or object therein;

a processor; and a wireless receiver communicatively coupled with the processor, the wireless receiver for wirelessly communicating with at least one sensor device located in the at least one storage volume of the at least one package, to wirelessly monitor the presence of at least one of the sanitizing agent comprising ozone and ultraviolet radiation energy in the at least one storage volume thereby monitoring exposure of the product and/or object being stored in the at least one storage volume to the at least one of the sanitizing agent comprising ozone and the ultraviolet radiation energy.

11. The package storage system of claim 10, further comprising:

a user interface, communicatively coupled with the processor, for providing to a user information indicating the status of detection of the presence of at least one of the sanitizing agent comprising ozone and ultraviolet radiation energy in the at least one storage volume of the at least one package.

12. The package storage system of claim 10, further comprising:

a database, communicatively coupled with the processor, for storing wirelessly monitored information indicating the status of detection of the presence of at least one of the sanitizing agent comprising ozone and ultraviolet radiation energy in the at least one storage volume of the at least one package.

13. The package storage system of claim 10, wherein the storage container for containing a plurality of packages, each of the plurality of packages having a packaging structure comprising packaging material providing at least one storage volume for receiving at least one product and/or object therein, the at least one storage volume of each of the plurality of packages for containing a first agent that is energizably convertible by an energy source to a sanitizing agent comprising ozone in the at least one storage volume, the sanitizing agent comprising ozone being transferable from the at least one storage volume to the product and/or object therein to provide at least one of a sanitizing, disinfecting, and sterilizing, application to the product and/or object, and wherein the wireless receiver for wirelessly communicating with at least one sensor device located in the at least one storage volume of each of the plurality of packages, to wirelessly monitor the presence of at least one of the sanitizing agent comprising ozone and ultraviolet radiation energy in the at least one storage volume of each of the plurality of packages thereby monitoring exposure of the at least one product and/or object being stored therein to the at least one of the sanitizing agent comprising ozone and the ultraviolet radiation energy, and further wherein the at least one sensor device comprises an RF ID device being wirelessly readable from the wireless reader device to uniquely identify one of the plurality of packages that contains a particular product and/or object from the other of the plurality of packages.

14. The package storage system of claim 13, wherein the at least one sensor device in each of the plurality of packages comprising an RF ID device, and the processor being configured to operate with the wireless receiver as a wireless RF ID reader, for the processor to wirelessly monitor the presence of at least one of the sanitizing agent comprising ozone and ultraviolet radiation energy in the at least one storage volume of each of the plurality of packages and to uniquely identify each of the plurality of packages contained in the storage container, using RF ID wireless communication technology and protocol.

15. A self-monitoring package arrangement comprising:

a packaging container for receiving products and/or objects therein, the packaging container having a packaging structure comprising packaging material providing at least one storage volume, the at least one storage volume for containing a first agent that is energizably convertible by an energy source to a sanitizing agent comprising ozone in the at least one storage volume, the sanitizing agent comprising ozone being transferable from the at least one storage volume to a product and/or object in the packaging container to provide at least one of a sanitizing, disinfecting, and sterilizing, application to the product and/or object; and at least one sensor device, located in the at least one storage volume, with one or more of the at least one sensor device each comprising an ultraviolet radiation sensor located in close proximity to an inside surface of the packaging material of the packaging structure providing the at least one storage volume of the packaging container and the ultraviolet radiation sensor being oriented substantially toward the nearest inside surface of the packaging material of the packaging structure providing the at least one storage volume to detect ultraviolet radiation energy radiated through the packaging material and into the at least one storage volume, to monitor the presence of at least one of the sanitizing agent comprising ozone and ultraviolet radiation energy in the at least one storage volume thereby monitoring exposure of the product and/or object in the packaging container to the at least one of the sanitizing agent comprising ozone and the ultraviolet radiation energy, and further wherein the at least one sensor device comprising an RF ID device and being wirelessly readable from a wireless RF ID reader to uniquely identify a packaging container that contains a particular product and/or object.

16. The self-monitoring package arrangement of claim 15, wherein the ultraviolet radiation energy in the at least one storage volume comprising ultraviolet radiation energy being radiated in the at least one storage volume by an ultraviolet radiation energy source located outside of the packaging container, the at least one sensor device being mechanically coupled to an inside surface of the at least one storage volume and oriented in the at least one storage volume to monitor the presence in the at least one storage volume of the at least one of
the sanitizing agent comprising ozone, and
the ultraviolet radiation energy from the ultraviolet radiation energy source located outside of the packaging container.

17. The self-monitoring package arrangement of claim 15, wherein the at least one sensor device comprises one or more open space extensions that provide at least one gap space arrangement to provide gap space near a sensor of the at least one sensor device and to separate the sensor from an adjacent surface of a product and/or object stored in the at least one storage volume and contacting the one or more open space extensions where one of the at least one sensor device is located and thereby monitoring the presence of, and the exposure of the product and/or object to the sanitizing agent comprising ozone in the at least one storage volume.

18. The self-monitoring package arrangement of claim 15, wherein the at least one sensor device comprising a sensor device module including:
a substrate; and
at least one sensor mechanically coupled to the substrate, the at least one sensor for monitoring the presence of the at least one of the sanitizing agent comprising ozone and the ultraviolet radiation energy in the at least one storage volume; and wherein:
the sensor device module being unattached to any inside surface of the packaging material of the packaging structure providing the at least one storage volume, in unrestricted location inside the at least one storage volume and thereby freely locatable in the at least one storage volume without direct physical contact restriction to any particular inside surface of the at least one storage volume.

19. The self-monitoring package arrangement of claim 1, wherein the first agent comprises oxygen and the first agent is energizably convertible to the sanitizing agent comprising ozone by the energy source at a first state of the energy source, and wherein the sanitizing agent comprising ozone is energizably convertible to the first agent comprising oxygen by the energy source at a second state of the energy source, and wherein the at least one sensor device being incorporated in the packaging material and packaging structure of the packaging container and thereby integrally coupled to an inside surface of the at least one storage volume for monitoring the presence of at least one of the sanitizing agent comprising ozone, ultraviolet radiation energy from the energy source at the first state of the energy source, and ultraviolet radiation energy from the energy source at the second state of the energy source, in the at least one storage volume, and further wherein the at least one sensor device comprising an RF ID device that is wirelessly readable by a wireless RF ID reader device to uniquely identify a packaging container that contains a particular product and/or object.

20. A package storage system, comprising:
a storage container for containing at least one package in a first storage volume in the storage container, the at least one package including at least one storage volume for receiving a product and/or object therein, the at least one storage volume for containing a first agent that is energizably convertible by an energy source to a sanitizing agent comprising ozone in the at least one storage volume, the sanitizing agent comprising ozone being transferable from the at least one storage volume to the product and/or object to provide at least one of a sanitizing, disinfecting, and sterilizing, application to the product and/or object;
at least one sensor device being located in the at least one storage volume of the at least one package, with one or more of the at least one sensor device each comprising an ultraviolet radiation sensor located in close proximity to an inside surface of packaging material of the at least one storage volume of the at least one package and the ultraviolet radiation sensor being oriented toward the nearest inside surface of the packaging material of the at least one storage volume to detect ultraviolet radiation energy radiated through the packaging material and into the at least one storage volume, to monitor the presence of at least one of the sanitizing agent comprising ozone and ultraviolet radiation energy in the at least one storage volume thereby monitoring exposure of the product and/or object being stored in the at least one storage volume to the at least one of the sanitizing agent comprising ozone and the ultraviolet radiation energy;
at least one ultraviolet radiation energy source in the storage container, the at least one ultraviolet radiation energy source being energizable to provide first ultraviolet radiation energy through the packaging material and in the at least one storage volume of the at least one package for energizably converting the first agent to a sanitizing agent comprising ozone in the at least one storage volume, and further being energizable to provide second ultraviolet radiation energy through the packaging material and in the at least one storage volume and that delivers anti-microbial ultraviolet energy to exposed surfaces of the product and/or object in the at least one storage volume of the at least one package;
a processor;
a wireless receiver, communicatively coupled with the processor, the wireless receiver for wirelessly communicating with at least one sensor device located in the at least one storage volume of the at least one package and that senses the presence of at least one of the sanitizing agent comprising ozone, the first ultraviolet radiation energy, and the second ultraviolet radiation energy, in the at least one storage volume of the at least one package; and
a wireless reader device, communicatively coupled with the wireless receiver and the processor, being located outside of the at least one storage volume to wirelessly monitor the presence of at least one of the sanitizing agent comprising ozone, the first ultraviolet radiation energy, and the second ultraviolet radiation energy, in the at least one storage volume thereby monitoring exposure of the product and/or object in the at least one storage volume to the at least one of the sanitizing agent comprising ozone, the first ultraviolet radiation energy, and the second ultraviolet energy, and further wherein the at least one sensor device comprises an RF ID device being wirelessly readable from the wireless reader device to uniquely identify one of the at least one package that contains a particular product and/or object, from another of the at least one package, and to monitor a detection status of the presence of at least one of the sanitizing agent comprising ozone and ultraviolet radiation energy in the at least one storage volume, and wherein the at least one sensor device comprises one or more open space extensions that provide at least one gap space arrangement to provide gap space near a sensor of the at least one sensor device and to separate the sensor from an adjacent surface of at least one of a product and/or object or packaging material of the at least one storage volume contacting the one or more open space extensions to monitor the presence of the sanitizing agent comprising ozone using the sensor.

* * * * *